United States Patent [19]
Sinn et al.

[11] Patent Number: 5,622,685
[45] Date of Patent: Apr. 22, 1997

[54] POLYETHER-SUBSTITUTED PORPHYRIN ANTI-TUMOR AGENTS

[75] Inventors: Hans J. Sinn, Wiesloch; Hans-Hermann Schrenk, Zeiskam; Wolfgang Maier-Borst, Dossenheim; Eckhard Friedrich, Ilbesheim; Georgi Graschew, Wiesloch; Dieter Wohrle, Bremen; Thomas Klenner, Hirschberg, all of Germany

[73] Assignee: Deutches Krebsforchunszentrum Stiftung des Offentlichen Rechts, Germany

[21] Appl. No.: 472,765

[22] Filed: Jun. 7, 1995

Related U.S. Application Data

[63] Continuation of Ser. No. 828,818, filed as PCT/EP91/00992, May 29, 1991, abandoned.

[30] Foreign Application Priority Data

May 30, 1990 [DE] Germany .................. 40 17 439.5

[51] Int. Cl.⁶ .................. A61K 51/02; C07D 487/22
[52] U.S. Cl. .................. 424/1.65; 424/1.85; 424/9.61; 540/145; 540/122; 540/121; 514/410
[58] Field of Search .................. 424/1.65, 1.85, 424/9.61; 540/145, 121, 122; 514/410

[56] References Cited

U.S. PATENT DOCUMENTS

| | | | |
|---|---|---|---|
| 5,053,423 | 10/1991 | Liu | 514/410 |
| 5,109,016 | 4/1992 | Dixon et al. | 514/410 |
| 5,162,231 | 11/1992 | Cole et al. | 436/64 |
| 5,162,519 | 11/1992 | Bonnett et al. | 540/145 |
| 5,284,647 | 2/1994 | Niedballa et al. | 424/81 |

FOREIGN PATENT DOCUMENTS

| | | |
|---|---|---|
| 63-154689 | 10/1987 | Japan. |
| 62-249986 | 6/1988 | Japan. |
| 0304311 | 2/1989 | United Kingdom. |
| 9015628 | 12/1990 | WIPO .................. A61K 47/48 |

OTHER PUBLICATIONS

Sigma Catalogue, p. 671, 1994.
Inada et al., JP 63154689 as abstracted in *Chemical Abstracts*, CA 111(9): 70956a, 1988.
Suzuki et al., "Preparation of Cyclotriphosphazene derivatives Bound to Hydrophilic Polymer & Therapeutic Physiologically Active Substrate" *Chemical Abstract* vol. 112, No. 3, 1990, p. 519. AB. #21146y.

*Primary Examiner*—Gary E. Hollinden
*Assistant Examiner*—Lara E. Chapman
*Attorney, Agent, or Firm*—Venable, Baetjer, Howard & Civiletti, LLP

[57] ABSTRACT

Tumor-active or tumor-diagnostic substances having preferred accumulation in the tumor, which are characterized in that they have

- at least two phenolic hydroxyl and/or amino groups,
- at least one aliphatic amino group, or
- at least one phenolic hydroxyl and/or amino group and
- at least one aliphatic amino group and that these groups are substituted with polyethylene glycol chains whose polymerization degree n is 5 to 250 and whose terminal hydroxyl group is substituted by $C_1$–$C_{12}$ alkyl ester or ether, each of the substances being substituted by at least two such polyethylene glycol chains.

14 Claims, 5 Drawing Sheets

POLYETHER-SUBSTITUTED PORPHYRIN ANTI-TUMOR AGENTS

This application is a continuation of application Ser. No. 07/828,818, filed Mar. 30, 1992, now abandoned, which is a 371 of PCT EP91/0092, filed May 29, 1991 which claims priority to German Patent applications DE P-4017439.5, filed May 30, 1990.

The present invention relates to polyether-substituted anti-tumor agents, namely the use of polyethers as new synthetic carrier systems serving for infiltrating tremors with low-molecular compounds so as to improve the in vivo tumor diagnosis and tumor therapy using different clinical procedures.

The substances presently employed for diagnostic and therapeutic use in the detection and treatment of tumors are usually low-molecular and are concentrated specifically by the neoplastic tissues only in exceptional cases. Typical examples of low-molecular pharmaceutical preparations are:

1. cis-platin compounds, tetracyclines, steroids and the like for chemotherapy,
2. porphyrins, phthalocyanines and naphthalocyanines for laser-induced fluorescence diagnosis and photodynamic therapy (PDT),
3. conventional X-ray contrast agents such as gadolinium DTPA (a low-molecular metal complex) for computerized tomography (CT) or magnetic resonance tomography (MRT).

In order to obtain the high concentration of a preparation employed, which is necessary at the desired site, e.g. the substance concentrations required in the tumor tissue, high initial amounts of compound have to be applied, if possible at all on account of the toxicity of the preparations. In principle, photodynamic therapy (PDT) and chemotherapy are based upon the effect which less than 1% of the total dose administered has on the tumor tissue when these substances are applied systemically. Thus, since usually less than 1% of the applied dose reach the tumor, the other 99% represent an undesired but unavoidable stress for the healthy organs, above all for liver and kidneys.

Therefore, a need has existed in pharmacology for a long time to directly transport preparations to the site where they are actually needed so as to arrange for the necessary high concentration there without simultaneously stressing the other organs considerably.

Figure 1:
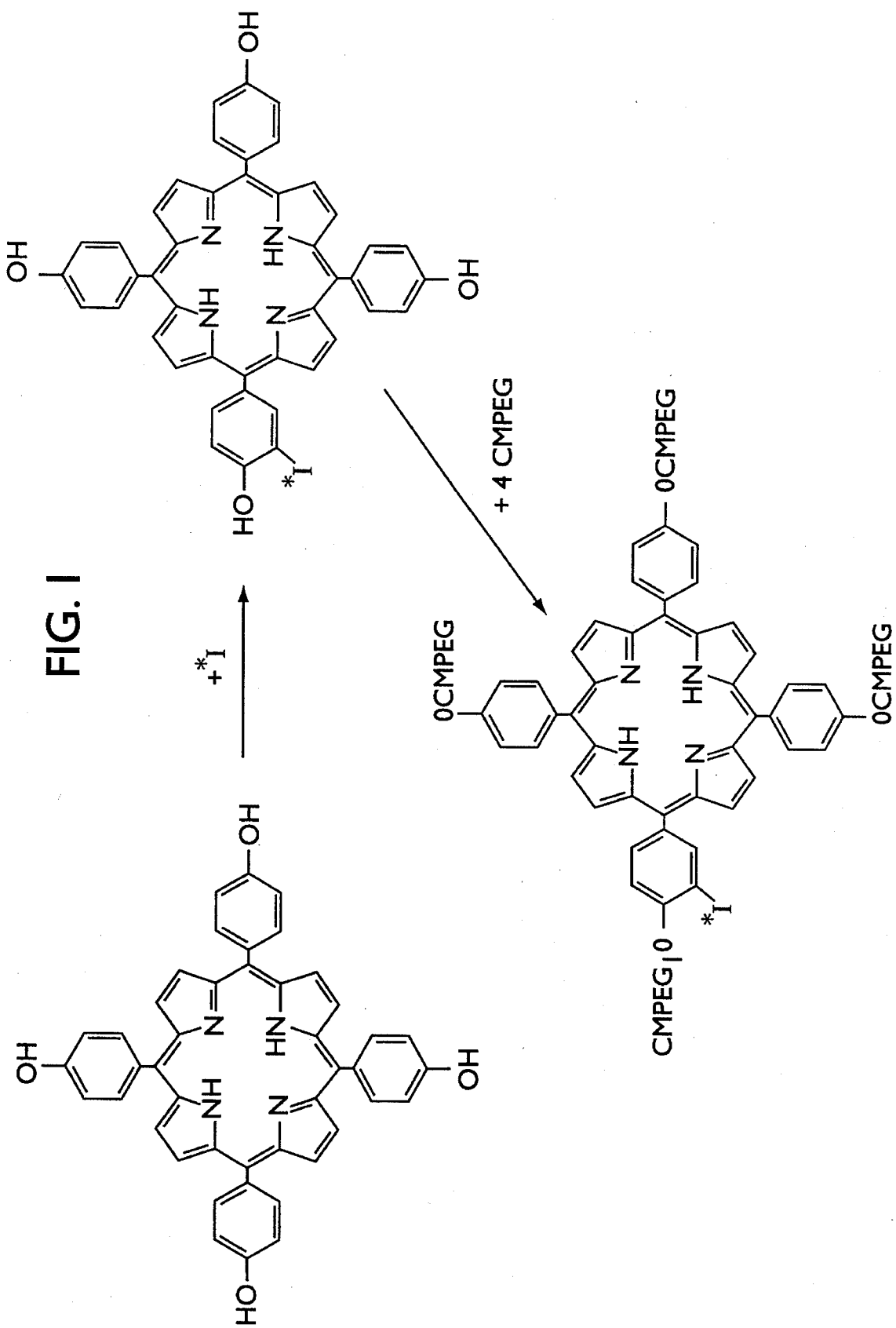
FIG. 1 shows reaction formulae for radioiodine labeling and CMPEG derivatization of: 5,10,15,10-tetrakis(4-hydroxyphenyl)-21H,23H-porphin.

The present invention solves this problem by derivatizing aromatic hydroxyl and/or amino groups with polyethylene glycols whose terminal hydroxyl group is etherified or esterified with $C_1$–$C_{12}$ alkyl groups, a certain preference existing for the $C_1$–$C_8$, particularly $C_1$ and $C_6$, alkyl group as well as for the $C_{10}$ and $C_{12}$ alkyl group. However, the methoxy group is the most preferred one. In the case of the methoxypolyethylene glycols (MPEG) chain lengths of 5 to 250 ethylene oxide units, i.e. n=5 to 250, are used, preferably chains having n=10 to 200. This means that the polyethylene glycol residue including the methoxy group, wherein the polyethylene glycol chain may, of course, be branched as well, has a molecular weight of about 250 to about 11,000 (n=5 to 250), particularly about 470 to little less than 9,000 (n=10 to 200). Since at least two such terminally substituted polyethylene glycol chains are attached to the compound to be derivatized, its chain length has to be chosen such that the desired total molecular weight results. Methoxypolyethylene glycols having a molecular weight of about 5,000 are particularly preferred. If a total molecular weight of over 10,000 is desired or particularly if the polyethylene glycol chain per se already has a relatively high molecular weight which is little less than or over 10,000, activation will be effected by means of cyanuric chloride in a manner known per se to carry out the derivatization. Methoxypolyethylene glycols activated in such a way by cyanuric chloride are referred to as CMPEG herein.

In the compound to be derivatized, usually a cytostatic agent or a compound suitable for diagnosis, it is possible to use, along with phenolic hydroxyl and/or amino groups, at least two of which should be present, aliphatic amino groups of such low-molecular pharmaceutical compounds for this derivatization. However, the amino groups are not suitable for O-iodine compounds, since iodine is otherwise displaced or separated.

Thus, a derivative according to the invention comprises at least two phenolic hydroxyl and/or amino groups, at least one aliphatic amino group, or at least one phenolic hydroxyl and/or amino group and at least one aliphatic amino group. These groups are substituted with polyethylene glycol chains whose polymerization degree n is 5 to 250 and whose terminal hydroxyl group is substituted by $C_1$–$C_{12}$ alkyl ester or ether. In this case, a derivative according to the invention is substituted by at least 2 such polyethylene glycol chains.

Total molecular weights of 10,000 or more, which the cytostatic agents derivatized with polyethylene glycol residues have, are markedly preferred, since it is not so easy for the kidneys to excrete compounds of this range (a molecular weight of about 20,000 represents the exclusion limit of the kidneys).

Thus, if 4 polyethylene glycol residues are bound and the molecular weight is to be somewhat above 10,000, the molecular weight of each polyethylene oxide chain (the methoxy or alkoxy or ester group is neglected herein) shall be at least about 2,000 to 2,500 so as to result in a total molecular weight of about 10,000 for the derivatized compound.

Because of the chain length of the polyethylene glycol chain or its branch, a total block forms with serum albumin which is capable of staying in the body, cannot be excreted easily as usual and focuses well on the tumor to be treated or diagnosed.

Due to this block formation with serum albumin it is not required that the total molecular weight of the compounds to be derivatized, including the polyethylene glycol chains, is over 20,000 although such high molecular weights can, of course, be chosen as well if one does not want to rely on this block formation with serum albumin. For example, the incorporation of four of the preferred methoxypolyalkylene glycol chains having a molecular weight of about 5,000 into a compound to be derivatized results in a total molecular weight of about 20,000.

It is well known to attach polyethylene glycol to the most varying substances so as to achieve certain effects. In J. Biol. Chem. 252, 3578, (1977), Abuchowski et al. describe the change of immunological properties of bovine serum albumin by the covalent bond of polyethylene glycol. In Analytical Biochemistry 131, 25, (1983), Beauchamp et al. show a synthesis of polyethylene glycol protein adducts as well as effects on the function, receptor detection and clearance of peroxide dismutase, lactoferrin and alpha-2-macroglobulin. In TIBTECH, July 1966, 190, Inada et al. show the use of polyethylene glycol-modified enzymes in biotechnological processes, namely enzymes soluble in organic solvents. In Biochem. and BioPhys. Res. Communications, 138, 283 (1986), Takahashi et al. show polyethylene glycol-modified hemin having peroxidase activity in organic solvents. In Analytical Biochemistry 165, 114, (1987), Jackson et al. describe the synthesis, isolation and characterization of conjugates of ovalbumin by monomethoxypolyethylene glycol using cyanuric chloride as a coupling agent, and in Biochemica et Biophysica Acta 198, 276, (1970), Kay and Lilly show the chemical bond of chymotrypsin to give water-insoluble polymers using 2-amino-4,6-dichloro-s-triazine.

However, none of these studies deals with the problem under consideration herein which is of importance particularly for the treatment of tumors.

The derivatization of the compound with MPEG or CMPEG serves for 1. generally producing an increase in hydrophilia, a high degree of water solubility being achieved in the physiological pH range;
2. producing a strong bond to plasmaproteins, which considerably delays in particular the excretion of the kidneys;
3. achieving a suppression of the detection and trapping mechanisms in the liver with respect to foreign substances; and
4. obtaining a substantial increase in the stability of iodine-containing compounds.

As a result, the following advantages are possible:

1. The generation of a high degree of hydrophilia (water solubility) of all substances implies that all compounds are readily usable in isotonic aqueous media without any further solutizers.
2. A strong bond of the MPEG or CMPEG derivatives to plasma proteins prevents rapid excretion of the foreign substances via the kidneys.
3. The suppression of the detection and trapping mechanisms in the liver in combination with the suppressed kidney excretion guarantees a long residence time in the blood, which simultaneously results in considerably increased accumulations in the tumor.
4. The stabilization of (radioactive) iodine-containing compounds prevents the separation of (radioactive) iodine in the organism, which is of major importance for reducing the radiation exposure of the thyroid gland to radioactive iodine, on the one hand, and implies considerably reduced risks in patients suffering from iodine allergy, on the other.
5. The substantial increase in tumor accumulation rates (in animal experiments usually 30%, and up to 50% or more of the total dose applied) permit a general reduction of the substance amounts necessary for diagnostic or therapeutic measures, which in turn results in a reduction of the total-body stress. In the case of the rapidly growing melanoma, a concentration of 80% of active substance has already been observed in the region to be treated.

The accumulation which, particularly with the radioactively labeled substances, shows markedly in the images is outstandingly surprising. It is now possible to directly transport substances to the specific site, particularly for the diagnosis and therapy of tumors.

Figure 2:
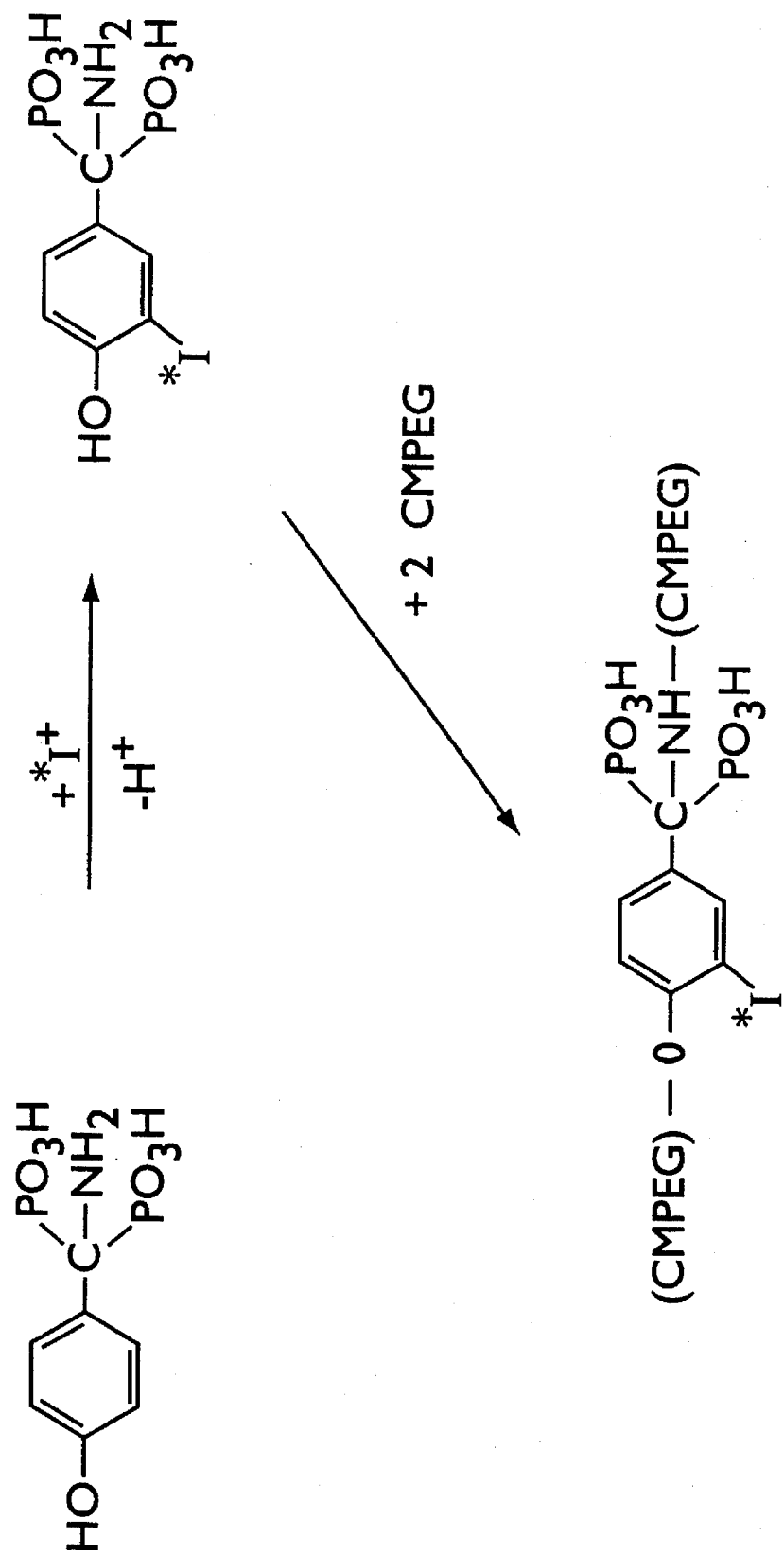
FIG. 2 shows reaction formulae for radioiodine labeling and CMPEG derivatization of: p-hydroxyphenyl-1-aminomethane-1,1-diphosphonic acid.
Figure 3:
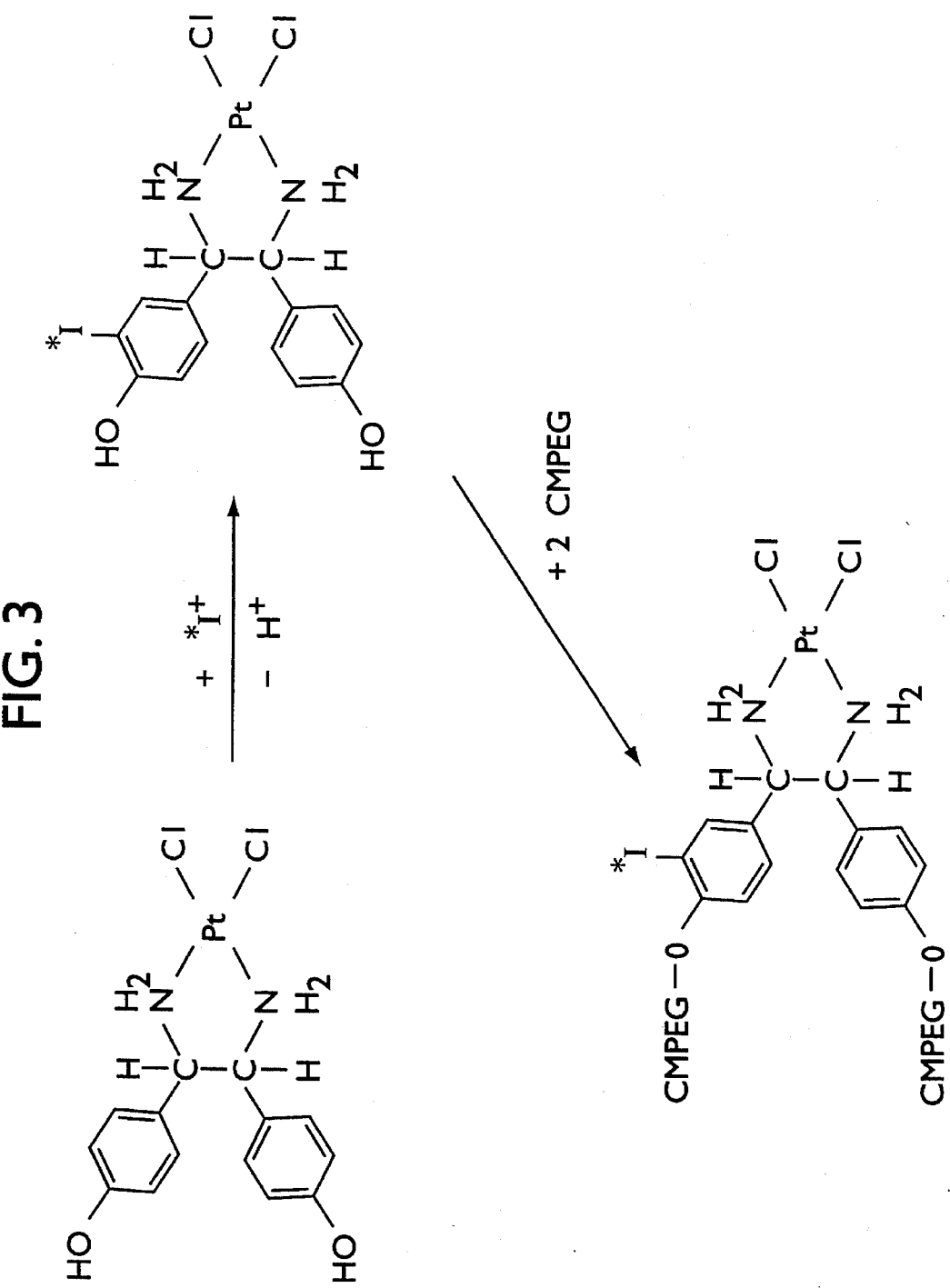
FIG. 3 shows reaction formulae for radioiodine labeling and CMPEG derivatization of: 1,2-bis(4-hydroxyphenyl)-1,2-diamino-ethane-cis-platin-II-chloride.

Examples of polyether-derivatized substances, all of which have a high specific accumulation rate in the tumor tissue and result in a considerably reduced stress of normal tissues or organs, as well as their possible uses are given below:

1. Porphins, phthalocyanines and naphthalocyanines, which are known as regards their type, for the laser-induced fluorescence diagnosis and photodynamic therapy (PDT) of tumors. As radioiodine-labeled compound for nuclear-medical localization of unknown metastases, for determining the optimum time for a PDT as well as for a possible radioiodine therapy. Reaction formulae for radioiodine labeling as well as CMPEG derivatization are shown in FIG. 1 for 5,10,15,20-tetrakis(4-hydroxyphenyl)-21H,23H-porphin.
2. Radioiodine-labeled diphosphonates for nuclear-medical localization of tumors and/or metastases or their radioiodine therapy. Reaction formulae for radioiodine labeling as well as CMPEG derivatization are shown in FIG. 2 for p-hydroxyphenyl-1-aminomethane-1,1-diphosphonic acid.
3. Cis-platin and cis-platin derivatives, tetracyclines and steroids as well as similar compounds for chemotherapy. Radioiodine-labeled products serve for the nuclear-medical detection of the individual substance distribution patterns. Reaction formulae for radioiodine labeling as well as CMPEG derivatization are shown in FIG. 3 for 1,2-bis(4-hydroxyphenyl)-1,2-diaminoethane-cis-platin-II-chloride.
4. Peptides, porphins, phthalocyanines, naphthalocyanines and similar compounds, which are labeled with radioiodine, radiobromine or radioactive metal ions, for the positive representation of tumors using a gamma camera imaging in a plane or tomographically.
5. Highly iodinated compounds such as: porphins, oligomeric tyrosines, etc., for the positive representation of tumors by means of computerized tomography (CT).
6. Metal complexes such as: gadolinium phthalocyanines for positive tumor representation by means of magnetic resonance tomography (MRT).
7. Radiosensitizers such as: nitroimidazole as a support for the radiotherapy of tumors using external or tumor-incorporated radiation sources, e.g. in PDT which is discussed above under point 1.
8. Luminols for the intratumoral production of chemiluminescence and their use for direct phototherapy of neoplastic tissues.
9. Boric acid esters for the neutron trapping therapy of tumors.
10. Dysprosium 164 for phthalocyanines (not for porphyrins, for example, since Dy is too great for them). $Dy^{164}$ the last stable isotope traps thermal neutrons and emits β thereby changing into $Ho^{165}$.

The polyethylene glycol residues are such that the total compounds have a molecular weight of 2,000 to 10,000 or above. Since at least two such residues are to be attached to the cytostatic agent, this results in a minimum molecular weight of little less than 1,000 for the methoxypolyethylene glycols, for example. A molecular weight of about 5,000 is especially preferred. In the case of these polyethylene oxide residues a terminal hydroxyl is substituted by a $C_1$-$C_{12}$ alkyl ether or ester group. The methoxy compound is preferred in this case. Methoxypolyethylene oxides having a molecular weight of about 5,000 are commercially available and, possibly after conventional known purification, can be used directly for the synthesis of the cytostatic agent derivatives according to the invention. If such an agent is to be labeled with iodine, for example, the iodine atom will first be introduced and then the polyoxyethylene chain is attached as usual by means of a linker, preferably cyanuric chloride.

The total molecular weight of the cytostatic agent derivatives according to the invention is preferably more than 10,000. If, for example, a porphin according to FIG. 1 is used whose molecular weight is about 678, 4 methoxypolyethylene oxide residues having a molecular weight of about 5,000, but at least about 2,500, will be attached in this case.

In the case of the compound according to FIG. 2, i.e. the diphosphonic acid compound shown, two methoxypolyethylene oxide residues having a molecular weight of about 5,000, or even better 6,000, should be attached.

Because of the chain length and/or the branch of the chain, this polyethylene glycol substitution permits the formation of a total block with serum albumin, whose size exceeds the exclusion limit of the kidneys, as mentioned above.

If the preparation is a phthalocyanine, the concentration of this preparation administered is so high in the tumor that the tumor is seen in a blue color. It is of interest that the coloring matter only accumulates in vital tumor tissue but not in necrotic tissue as shown by enclosed FIG. 4.

The following examples serve for explaining the invention and describe the production of the derivatized cytostatic agents:

EXAMPLE 1

Production of radioiodine-labeled and CMPEG-derivatized TOP

100 μg of tetra-(4-hydroxyphenyl)-porphin (TOP), dissolved in 100 μg of dimethylacetamide, are admixed with 5–20 μl of an alkaline solution (pH 8–11) of radioiodine (iodide) having an activity of 18.5 MBq (500 μCi) to 185 MBq (mCi) and 3–10 μg of N-chlorosuccinimide (NClS), dissolved in 2–5 μl of acetonitrile. After a reaction period of 20–30 min, 4 mg of alpha-dichlorotriazine-Ω-methoxypolyethylene glycol (n=100–110, i.e. 100–110 ethylene glycol units), dissolved in 40 μl of dioxan, and 100 μl of 0.17 M sodium bicarbonate solution are added. After a reaction period of 20–30 min, the reaction mixture is filled up with distilled water to 200 μl and the organic solvents are separated via an ultrafiltration unit having an exclusion limit of 5 kD. Attention has to be paid to the fact that an organic solvent having a high DK is used as the solvent.

Analytical chemistry:

Thin layer chromatography:

Plates: silica gel 60 (5×20 cm) (without fluorescent indicator)

eluent: methanol, 10% $NH_4$ acetate in water (1/1)

length of run: 10 cm

RF values: TOP 0.95–0.98 TOP-CMPEG 0.0

EXAMPLE 2

$^{131}$I labeling and CMPEG derivatization of: p-hydroxyphenyl-1-aminomethane-1,1-diphosphonic acid (HOPAD)

100 μl of a HOPAD solution in 0.17 M $NaHCO_3$ (1 mg/ml) are admixed with 2–5 mCi (74–185 MBq) of a $^{131}$I-Na-iodide solution (10–25 μl) and 3–7.5 μg of N-bromosuccinimide (NBS), dissolved in 0.17 M $NaHCO_3$ (1 mg/ml). The average $^{131}$I incorporation rate is 98% after a reaction period of 10 min at room temperature. Then, CMPEG dissolved in 1,4-dioxan (n=100–110) (100 mg/ml) is added in a molar ratio of 3:1 (about 5.5 mg). Non-bound $^{131}$I and non-derivatized HOPAD are separated by ultrafiltration or dialysis after a reaction period of about 30 min.

EXAMPLE 3

Preparation of tetra-(4 amino-phenoxy)-phthalocyanine-CMPEG (TAPPC-CMPEG)

A TAPPC solution (1 mg/ml) in tetrahydrofuran (THF) is admixed with five times the molar excess of CMPEG 5,000 (100 mg of CMPEG per ml of dioxan) and $NaHCO_3$ (0.13 M in water) at room temperature. After removing the major portion of the organic solvent under vacuum, the reaction mixture is diluted with distilled water and the reaction product is separated from the rest of the organic solvents, salts and water by means of ultrafiltration (exclusion limit 10,000 D). The new photosensitizer is ready for application after a second washing step and subsequent filtration sterilization.

It is essential that this photosensitizer has a very high photodynamic activity up to over 720 nm, with "bleaching" being hardly found.

EXAMPLE 4

Accumulation capacity of compounds according to the invention in tumors

The following compounds were investigated:

abbreviations:

TOP=tetra-(hydroxyphenyl)-porphin

TOPPC=tetra-(hydroxy-phenoxy)-phthalocyanine

TAPPC=tetra-(4 amino-phenoxy)-phthalocyanine-CMPEG

HOPAD=hydroxyphenyl-aminomethane-diphosphonate

HPBT=hematoporphyrin-bis-tyrimid

CMPEG=alpha-dichloro-triazine-Ω-methoxy-polyethylene glycol (n=100–110)

AMPEG=alpha-amino-Ω-methoxy-polyethylene glycol (n=100–110)

The following compounds were prepared in the same manner as described in Example 1 for $^{131}$I-tetra(hydroxyphenyl)-porphin-$(CMPEG)_4$ (1)a):

1)b $^{111}$In-tetra-(hydroxyphenyl)-porphin-$(CMPEG)_4$ 1)c $^{111}$In-tetra-(hydroxyphenoxy)-phthalocyanine-$(CMPEG)_4$, 1)d $^{131}$I-tetra-(hydroxyphenoxy)-phthalocyanine-$(DMPEG)_4$, 1)e $^{131}$I-hematoporphyrin-bis-tyrimid-$(CMPEG)_2$, and 1)f $^{131}$I-hydroxyphenyl-aminomethane-diphosphonate-$(CMPEG)_2$, all of which are used in nuclear medicine.

The following compounds were prepared correspondingly for use in fluorescence diagnosis and photodynamic therapy.

2a) TOP-(CMPEG)$_4$
2b) TOPPC-(CMPEG)$_4$
2d) HPBT-(CMPEG)$_2$.

The following compounds for NMR examinations were also prepared correspondingly:

3a) Mn-TOP-(CMPEG)$_4$
3b) Gd-TOPPC-(CMPEG)$_4$.

Finally, the following compounds were prepared according to Example 2 for CT scans:

4a) tri-iodine-phenol-CMPEG
4b) tri-iodine-benzoic acid-AMPEG
4c) iodoxaminic acid-(AMPEG)$_2$ The accumulation (concentration) of these preparations were examined in the following experimental tumors and the following experimental animals.

| Tumors | Experimental animal |
|---|---|
| a) experimental tumors | |
| ovarial carcinoma (0–342) | rat, BD IX |
| Walker carcinosarcoma | rat, Wistar |
| Yoshida hepatoma | rat, Wistar |
| Novikoff hepatoma | rat, Wistar |
| osteosarcoma | rat, SD curly |
| b) xenografts, human | |
| CX 1: colonic carcinoma | naked mouse |
| LX 1: axillary metastasis in a lymph node of a pulmonary carcinoma | naked mouse |
| MX 1: carcinoma of the breast | naked mouse |
| HS 1: osteosarcoma | naked mouse |
| MR I-H-186: carcinoma corpus uteri | naked mouse |
| HeLa: cervix carcinoma | naked mouse |
| EI 28: bladder carcinoma | naked mouse |
| GXF-96: gastric carcinoma | naked mouse |

All these experimental tumors and xenografts were examined with compounds a and c according to Example 1 (i.e. 1a and 1c) and three thereof, i.e. the Walker carcinosarcoma, the osteosarcoma and the ovarial carcinoma (O-342), were also examined with the diphosphonate according to Example 2.

Figure 4:
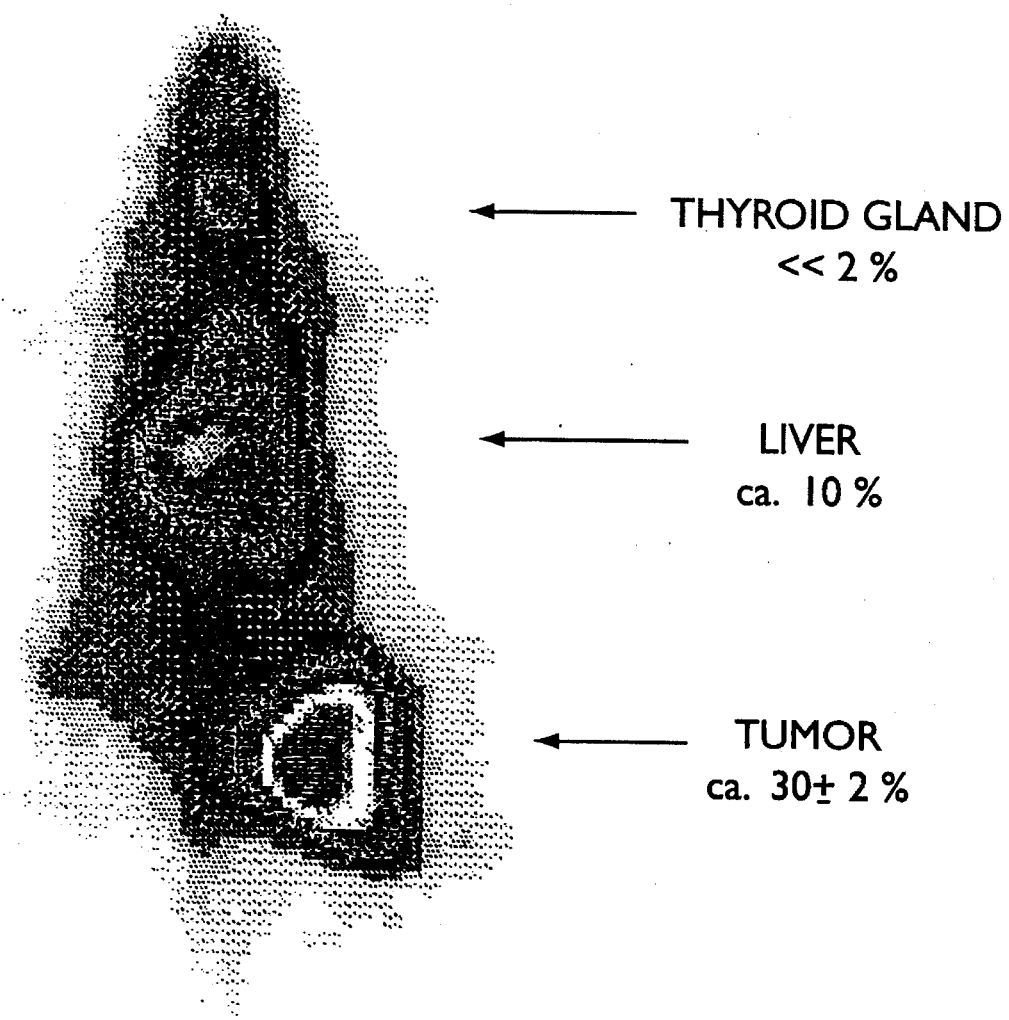
FIG. 4 shows the accumulation of $^{131}$I-labeled HOPAD-CMPEG (6.2) (p-hydroxyphenyl-1-aminomethane-1,1-diphosphonate-CMPEG) in the thyroid gland, liver and tumor of BD IX rats with ovarian carcinoma (O-342) 42 hours post-injection.

300 μC=11.1 MBq were always administered in all of these tests of application. With the preparations used, i.e. 1a and 1c and the compound of Example 2, a concentration of at least 30% of the preparation showed at the desired site, i.e. the tumor. Enclosed FIG. 4 shows the image of a BDIX rat having an ovarial carcinoma 42 h after the injection, which was treated with $^{131}$I-HOPAD-CMPEG, i.e. polyethylene glycol activated by $^{131}$I-hydroxyphenyl-1-aminomethane-1, 1-diphosphonate cyanuric chloride (n=about 100 to 110) in an amount of 300 μC. The image shows that, in the lower bottom, about 30 +/− 2% of the preparation are concentrated in the tumor, while, in the middle, the liver shows about 10% and the thyroid gland which is visible above the liver absorbed much less than 2% of the preparation. These percentages relate to the total amount of the radioiodine-labeled preparation in the total body of the rat.

When conventional cytostatic agents are administered, i.e. cytostatic agents that are not derivatized with polyethylene glycol derivative, a concentration in the tumor is standard that is about as high as that occurring in the thyroid gland, i.e. 0.05 to 0.5% of the total amount applied, with up to 90% of the amount administered being present in the liver, which, of course, results in an enormous stress of this organ, a stress that is not only undesired but also decidedly harmful.

Thus, the derivatization of common cytostatic agents having at least two phenolic hydroxyl and/or amino groups,
at least one aliphatic amino group, or
at least one phenolic hydroxyl and/or amino group and at least one aliphatic amino group, by polymolecular polyoxyethylene glycols with blocked terminal group results in a considerable concentration of the preparation in the vital tumor tissue and thus in a considerably improved effect at the desired site and a considerable relief of liver and thyroid gland, which, of course, markedly reduces the side-effects of such cytostatic agents.

Figure 5:
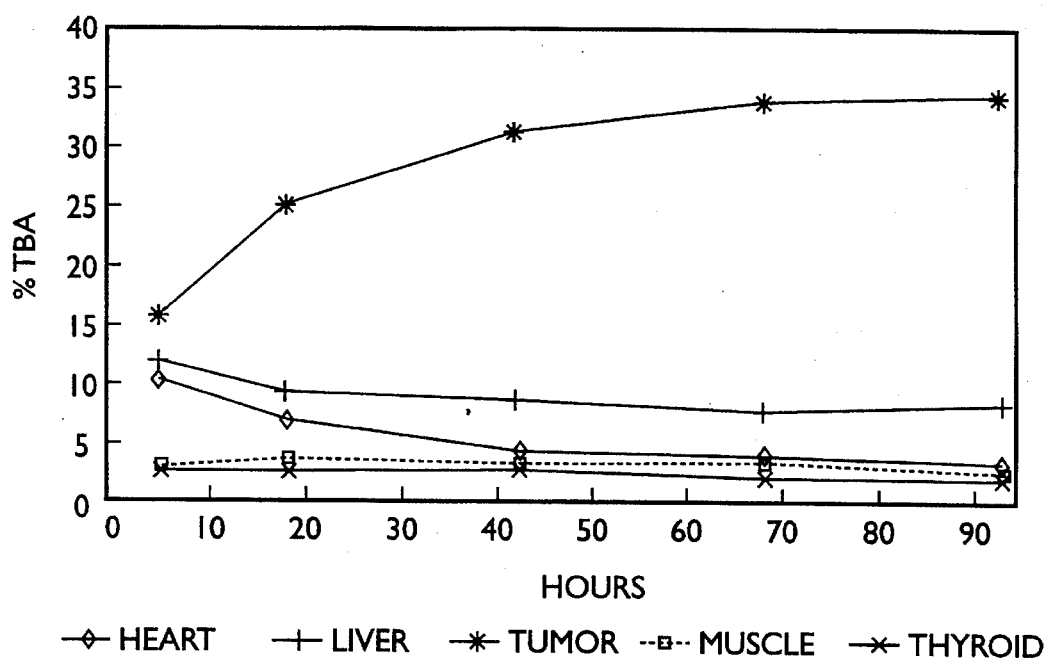
FIG. 5 shows the measurement of a BD IX rat with ovarian carcinoma treated with 131ITOP-(CMPEG)4. The accumulation of $^{131}$I in the indicated tissues is shown.

Enclosed FIG. 5 shows the measurement of a BD IX rat treated with $^{131}$I TOP-(CMPEG)$_4$ (here, too, ovarial carcinoma). A result similar as that of FIG. 4 shows.

After 150 h, about 23% of the entire body activity of radioactive iodine are found in the tumor, about 12% are found in the liver, about 5% in the blood and about 3–4% each in the muscles and the thyroid gland. The rest is, of course, spread over the rest of the body, as is also the case in the illustration of FIG. 4.

A high concentration in the tumor and a considerable relief of liver and thyroid gland are also found here, since with respect to this non-derivatized compound it also applies that upon administration thereof at most the amount as present in the thyroid gland is contained in the tumor.

We claim:

1. A tumor-active or tumor-diagnostic substance which exhibits preferred accumulation in the tumor, which comprises a substance substituted with polyethylene glycol chains, said substance selected from the group consisting of a porphin, a phthalocyanine and a naphthalocyanine and having (1) at least two groups selected from aromatic amino or phenolic hydroxyl groups or both, or (2) at least one aromatic amino or phenolic hydroxyl group or both, and at least one aliphatic amino group, said groups of (1) or (2) being substituted with polyethylene glycol chains whose polymerization degree n is 5 to 250 and whose terminal hydroxyl group is esterified or etherified with a $C_1$-$C_{12}$ alkyl, wherein the number of said polyethylene glycol chains attached to said substance is at least 3.

2. The substance of claim 1, wherein said substance is a porphin.

3. The substance of claim 2, wherein said porphin is tetra-(4-hydroxyphenyl)-porphin.

4. The substance of claim 1, wherein the polyethylene glycol chains have a polymerization degree n of 10 to 200.

5. The substance of claim 4, wherein said substance is a porphin.

6. The substance of claim 5, wherein said porphin is tetra-(4-hydroxyphenyl)-porphin.

7. The substance of claim 4, wherein the polymerization degree n is 100 to 110.

8. The substance of claim 7, wherein said substance is a porphin.

9. The substance of claim 8,, wherein said porphin is tetra-(4-hydroxyphenyl)-porphin.

10. A process for the preparation of the tumor-active or tumor-diagnostic substance of claim 1, comprising the steps of reacting the substance with an esterified or etherified polyethylene glycol in a suitable solvent and isolating the tumor-active or tumor-diagnostic substance.

11. The process of claim 10, wherein the reaction is activated by cyanuric chloride when polyethylene glycol chains having a molecular weight in the range of 5,000 Daltons to 11,000 Daltons are utilized.

12. A method for in situ diagnosis of tumor tissue, which comprises injecting into a subject the tumor-active or tumor-diagnostic substance of claim 1, wherein said substance is radioactively labeled with radioiodine or radiobromine, and detecting the site or sites of uptake of said substance by said tumor tissue.

13. A method for in situ diagnosis of tumor tissue, which comprises injecting into a subject the tumor-active or tumor-diagnostic substance of claim 1, wherein said substance is a porphin, and detecting the site or sites of uptake of said substance by said tumor tissue.

14. A method for in situ diagnosis of tumor tissue, which comprises injecting into a subject the tumor-active or tumor-diagnostic substance of claim 1, wherein said substance is tetra-(4-hydroxyphenyl)-porphin, and detecting the site or sites of uptake of said substance by said tumor tissue.

* * * * *

UNITED STATES PATENT AND TRADEMARK OFFICE
CERTIFICATE OF CORRECTION

PATENT NO. : 5,622,685

DATED : 22 April 1997

INVENTOR(S) : Hans-J. SINN et al.

It is certified that error appears in the above-identified patent and that said Letters Patent is hereby corrected as shown below:

On the title page: Item to read as follows: --

[73] Assignee:   Deutches Krebsforchungszentrum
                            Stiftung des Oeffentlichen Rechts,
                            Germany --

Signed and Sealed this

Ninth Day of December, 1997

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,622,685
DATED : April 22, 1997
INVENTOR(S) : Hans-J. Sinn, et. al.

It is certified that error appears in the above-identified patent and that said Letters Patent is hereby corrected as shown below:

ON THE TITLE PAGE:

Title page, item [75], inventor: should read -- Dieter Wöhrle --

Signed and Sealed this

Eighth Day of August, 2000

Attest:

Q. TODD DICKINSON

*Attesting Officer*         *Director of Patents and Trademarks*